(12) United States Patent
Bublewitz et al.

(10) Patent No.: US 9,463,079 B2
(45) Date of Patent: Oct. 11, 2016

(54) MIXER

(75) Inventors: Alexander Bublewitz, Herborn (DE); Jens-Peter Reber, Meinerzhagen (DE)

(73) Assignee: Kettenbach GmbH & Co. KG, Eschenburg (DE)

( * ) Notice: Subject to any disclaimer, the term of this patent is extended or adjusted under 35 U.S.C. 154(b) by 254 days.

(21) Appl. No.: 14/240,283

(22) PCT Filed: Aug. 10, 2012

(86) PCT No.: PCT/EP2012/065743
§ 371 (c)(1),
(2), (4) Date: Feb. 21, 2014

(87) PCT Pub. No.: WO2013/026722
PCT Pub. Date: Feb. 28, 2013

(65) Prior Publication Data
US 2014/0198602 A1  Jul. 17, 2014

(30) Foreign Application Priority Data

Aug. 24, 2011 (DE) .......................... 10 2011 111 046
Oct. 26, 2011 (WO) ................. PCT/EP2011/068784
Jul. 6, 2012 (DE) .......................... 10 2012 106 093

(51) Int. Cl.
*A61C 5/06* (2006.01)
*B01F 7/18* (2006.01)
(Continued)

(52) U.S. Cl.
CPC .............. *A61C 5/068* (2013.01); *A61C 5/064* (2013.01); *B01F 7/18* (2013.01); *B01F 13/0023* (2013.01); *B05C 17/00553* (2013.01);
(Continued)

(58) Field of Classification Search
CPC ... A61C 5/064; A61C 5/068; B01F 13/0023; B01F 2215/0027; B01F 2215/0039; B01F 7/00125; B01F 7/00141; B01F 7/18
See application file for complete search history.

(56) References Cited

U.S. PATENT DOCUMENTS 4,771,919 A * 9/1988 Ernst .................... B65D 81/325
222/134
4,986,820 A * 1/1991 Fischer ............. A61M 5/31513
604/218

(Continued)

FOREIGN PATENT DOCUMENTS

DE   10112904 A1   10/2002
DE   10164385 C1   3/2003
(Continued)

OTHER PUBLICATIONS

Form PCT/IB/338, Notification of Transmittal of Translation of the International Preliminary Report on Patentability, and wtih Form PCT/IPEA/409, Translated written opinon , total 6 pages. Mailed Feb. 24, 2014.

*Primary Examiner* — Tony G Soohoo
(74) *Attorney, Agent, or Firm* — McDonnell Boehnen Hulbert & Berghoff LLP

(57) ABSTRACT

The invention relates to a mixer (1) for mixing two components, in particular, a hardenable dental material. The mixer (1) has a mixer housing (2), a mixer element (4) and a cover (3). The mixer (1) has an annular chamber (17) that is in fluid communication with the mixing chamber of the mixer housing (2). The chamber (17) is defined by the cover (3), and by a plate (18) that is provided on the mixer element (4). The first of the inlet connections (12, 13) leading into mixer (1), ends in chamber (17), while the other ends downstream of plate (18) in the mixing chamber.

16 Claims, 4 Drawing Sheets

(51) Int. Cl.
  *B01F 13/00* (2006.01)
  *B05C 17/005* (2006.01)
  *B01F 7/00* (2006.01)

(52) U.S. Cl.
  CPC .... *B05C 17/00566* (2013.01); *B01F 7/00125* (2013.01); *B01F 7/00141* (2013.01); *B01F 2215/0027* (2013.01); *B01F 2215/0039* (2013.01)

(56) References Cited

U.S. PATENT DOCUMENTS

| | | | | |
|---|---|---|---|---|
| 5,033,650 | A * | 7/1991 | Colin | A61C 5/062 222/137 |
| 5,080,262 | A * | 1/1992 | Herold | A61C 5/064 222/135 |
| 5,333,760 | A * | 8/1994 | Simmen | A61C 5/064 222/135 |
| 6,523,992 | B1 * | 2/2003 | Bublewitz | A61C 5/064 222/145.6 |
| 6,837,612 | B2 | 1/2005 | Bublewitz et al. | |
| 7,287,898 | B2 * | 10/2007 | Pauser | B01F 15/0201 222/145.5 |
| 7,674,033 | B2 | 3/2010 | Pauser et al. | |
| 7,731,413 | B2 * | 6/2010 | Busin | B01F 5/0619 222/145.6 |
| 8,365,958 | B2 * | 2/2013 | Ho | B01F 5/0615 222/137 |
| 8,579,497 | B2 * | 11/2013 | Harre | A61C 5/064 222/145.6 |
| 2003/0123323 | A1 * | 7/2003 | Bublewitz | A61C 5/064 366/172.1 |
| 2004/0257909 | A1 * | 12/2004 | Pieroni | A61C 5/064 366/172.1 |
| 2005/0205606 | A1 * | 9/2005 | Nehren | B05C 17/00553 222/145.5 |
| 2005/0226095 | A1 * | 10/2005 | Wagner | B01F 7/00141 366/194 |
| 2007/0072146 | A1 * | 3/2007 | Pierson | A61C 5/062 433/90 |
| 2008/0083782 | A1 * | 4/2008 | Heusser | A61C 5/064 222/145.5 |
| 2008/0089173 | A1 * | 4/2008 | Lu | A61C 5/064 366/339 |
| 2008/0128454 | A1 * | 6/2008 | Beckett | B05C 17/00516 222/137 |
| 2009/0152300 | A1 * | 6/2009 | Hayman | A61C 5/062 222/145.6 |
| 2010/0256591 | A1 * | 10/2010 | Hoa | A61C 5/064 604/415 |
| 2011/0273956 | A1 * | 11/2011 | Habibi-Naini | B05C 17/00556 366/190 |
| 2013/0021869 | A1 * | 1/2013 | Gartmann | B01F 7/00125 366/279 |
| 2013/0329517 | A1 * | 12/2013 | Linne | A61C 9/0026 366/290 |
| 2015/0136806 | A1 * | 5/2015 | Jung | A61C 9/0026 222/145.5 |

FOREIGN PATENT DOCUMENTS

| | | |
|---|---|---|
| DE | 20302987 U1 | 4/2003 |
| DE | 102004008748 A1 | 9/2004 |
| EP | 1149627 A2 | 10/2001 |
| EP | 1458467 B1 | 9/2004 |
| EP | 1892033 A1 | 2/2008 |
| EP | 1943012 B1 | 1/2010 |
| EP | 2190563 B1 | 6/2010 |

* cited by examiner

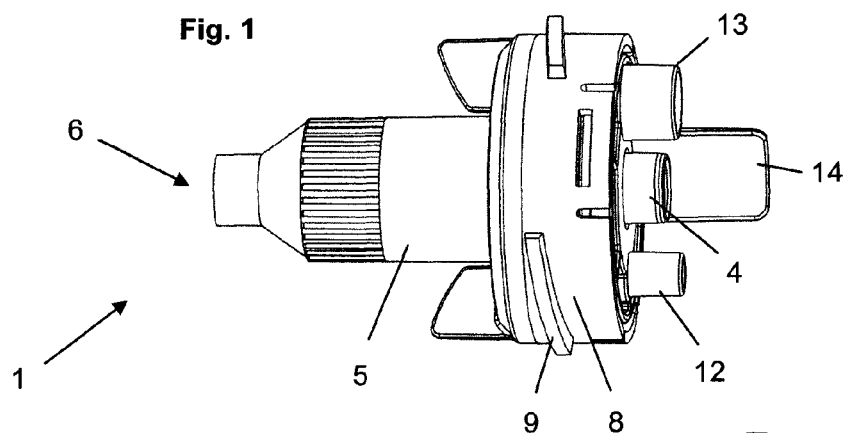
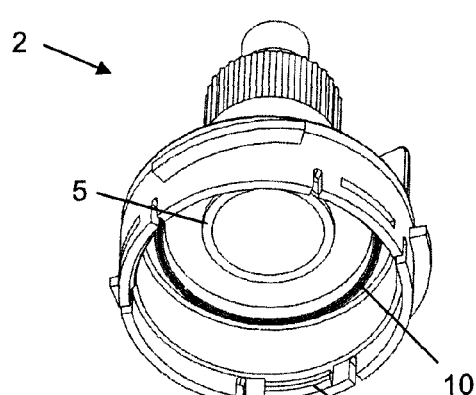
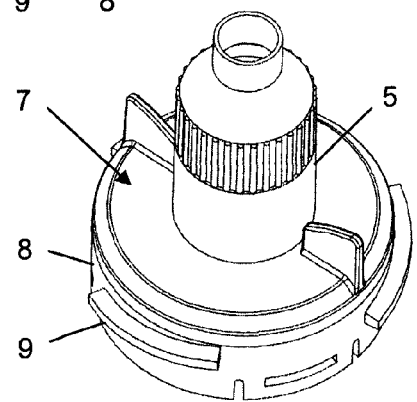
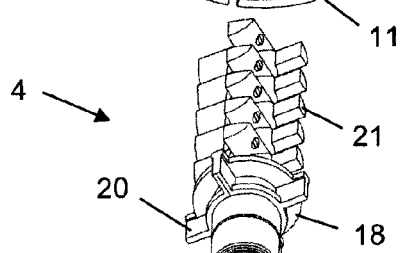
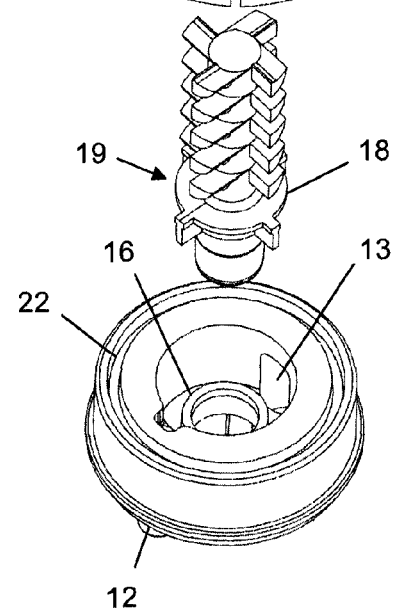
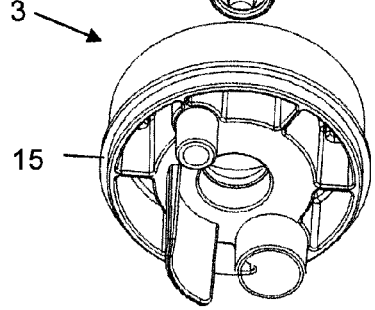
Fig. 1
Fig. 2
Fig. 3

Fig. 4
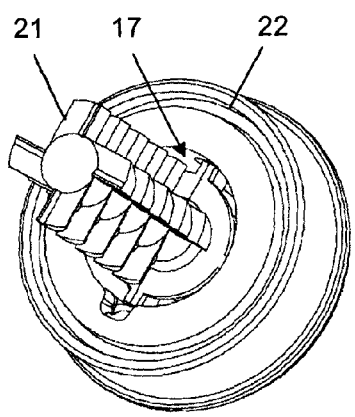
Fig. 6
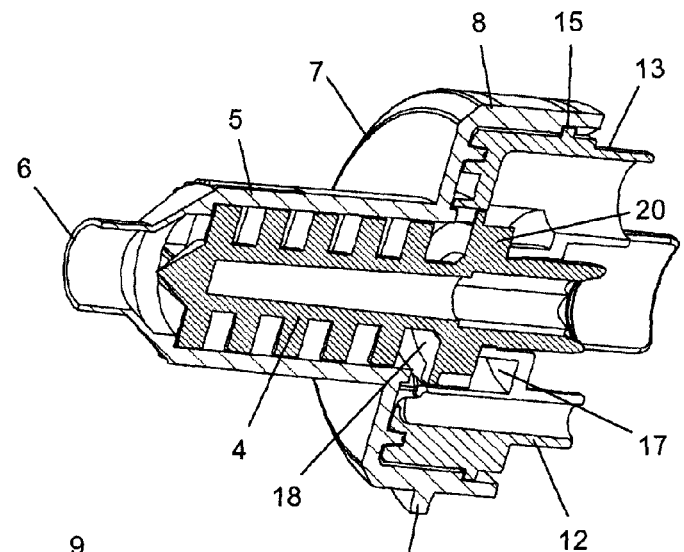
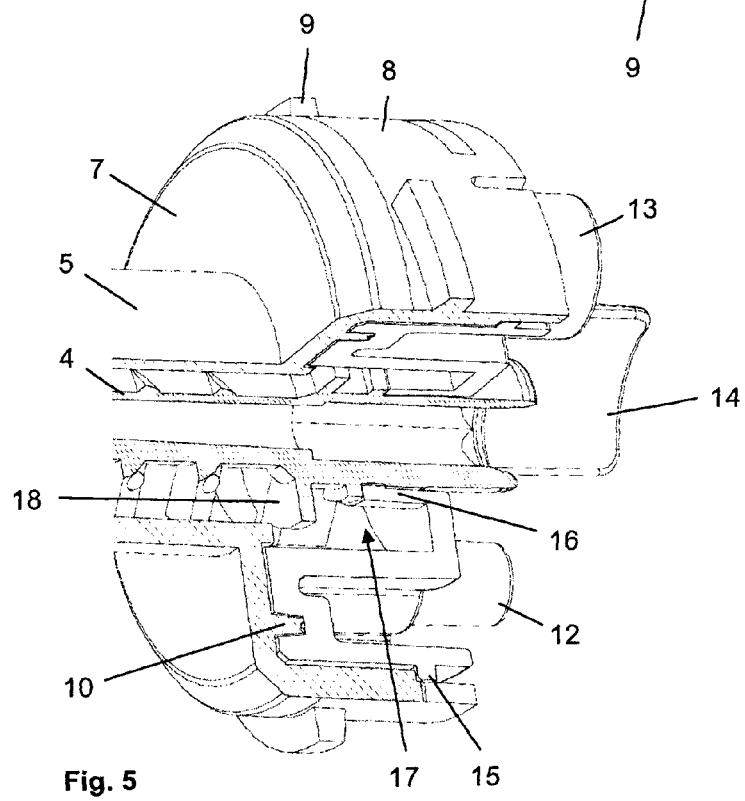
Fig. 5

MIXER

CROSS REFERENCE TO RELATED APPLICATIONS

The present application is a 35 U.S.C. 371 National Application of PCT/EP2012/065743 filed Aug. 10, 2012, which claims priority to German Patent Application No. 10 2011 111 046.5, filed Aug. 24, 2011, and National Application No. PCT/EP2011/068784, filed Oct. 26, 2011, and German Patent Application No. 10 2012 106 093.2, filed Jul. 6, 2012 the entire contents of which are incorporated entirely herein by reference.

The invention relates to a mixer for mixing two components, for example, components of a hardenable dental material. The mixer is formed primarily by a mixer housing, a mixer element and a cover. A mixing chamber with an outlet opening is located in the mixer housing. The mixer element extends into the mixing chamber and can be driven rotationally, in order to mix the components in the mixing chamber. The cover is connected with the mixer housing and has two inlet connections for the two components. In the mixer, an annular chamber is formed that is in fluid communication with the mixing chamber.

EP 1 943 012 B1 discloses a mixer of the type cited at the beginning, in which a mixer housing has an antechamber, a mixing chamber and a post mixing chamber. The two components that are to be mixed first arrive together in the antechamber, where they are distributed around the axis of rotation of the mixing rotor that is designed as a mixer element by means of a distribution body. The distribution body has a longitudinal cross section that is curved in the direction of the rotor hub. After being pre-mixed in the antechamber, the components can flow around the distribution body and arrive in the downstream mixing chamber, which is limited by a plate on the mixing rotor. This plate has slots, for example, through which the mixture can reach into the post mixing chamber located downstream of the mixing chamber.

When mixing two components, for example, for a dental material, a known problem consists therein, that one of the two components, most frequently the base component, tends to bleed relative to the other component (catalyst), so that a significant excess of the base component is present in the antechamber at the beginning of the mixing process. For this reason, an initial amount of mixture that is being discharged from the mixer is often discarded in practice, and only the mixture discharged from the mixer thereafter is used, for example, for an impression or the like.

DE 101 12 904 A1 and DE 10 2004 008 748 A1 therefore propose mixers in which in the flow path, a delay or accumulation chamber is provided between the inlet connections and the mixing chamber for the components tending to bleed that holds at least a part of the components that tend to bleed. The component that tends to bleed arrives in the mixing chamber only after this delay or accumulation chamber has been filled, as a result of which a better mixing ratio is established at the start of the mixing process. In the mixers known from DE 101 12 904 A1 or DE 10 2004 008 748 A1, the delay or accumulation chamber extends arched by almost 180° in a plane that is offset with the mixing chamber, while the other component (catalyst) is conveyed past the delay or accumulation chamber directly into the mixing chamber. It has been shown in practice that these known delay or accumulation chambers will fill completely with the components tending to bleed only then, when the actual mixing chamber is completely filled and thereby, a counter pressure is generated for the component tending to bleed. In this process, the improvement of the mixing ratio is not always reliable.

Further, from EP 1 1149 627 A2 and EP 2 190 563 B1 mixers are known in which both components arrive in the mixing chamber directly, without an upstream delay or accumulation chamber. Thereby, at the rotatable mixer element, basin-like elements are formed that are intended to prevent the components from flowing through the mixing chamber at a rapid rate. The problem of an insufficient mixing ratio for the components tending to bleed is not solved by these mixers.

From EP 1 458 467 B1, a mixer is known that has an axial delay chamber for one of the two components. The component is hereby conveyed through a knee, i.e. redirected in axial direction through a U-shaped piece. Although this leads to the desired delay of this component, it also increases the flow resistance of the mixer.

Furthermore, from EP 1 892 033 B1 a mixer is known that is simultaneously a dynamic mixer and a static mixer.

In contrast, it is the objective of the present invention to provide a mixer of the type cited at the beginning, in which the flow resistance for the components to be mixed is as low as possible, and an even mixing ratio can be established in the mixture discharging from the mixer from the start.

According to the invention, this problem is solved with a mixer as recited in Claim 1. Hereby, the chamber is preferably formed as an annular reservoir chamber that is defined by the cover and a plate that is provided on the mixer element. The first of the two inlet connections thereby ends in this annular reservoir chamber, while the second of the two inlet connections ends downstream of the plate in the mixing chamber. Thereby, the invention is based on the idea that in a mixer element that rotates in operation, i.e. in a dynamic mixer, the annular reservoir chamber is being filled with the component tending to bleed even then, when an adequate counter pressure is not yet present in the still empty mixing chamber. The component tending to bleed is thereby actively distributed by the rotating mixer element located in the annular reservoir chamber, so that the annular reservoir chamber fills up. By the spatially offset feed of the two components on the two opposite sides of the plate of the mixer element it is ensured that only the component tending to bleed is retained in the annular reservoir chamber, while in the mixing chamber, a uniform mixing ratio of the components is present from the start of the mixing process.

In order to achieve a flow resistance within the mixer that is as low as possible even with higher delivery speeds and/or more viscous components, the annular reservoir chamber and the inlet connections ending in it overlap at least partially in the axial direction of the mixer. In other words, the component arriving in the mixer through the first inlet connection can, at least partially, arrive in the annular reservoir chamber directly, without any redirection. It is preferred when the second inlet connection, or a channel that is attached to it, is designed in such a way that it ends in the mixing chamber in radial direction. This improves the mixing of the two components in the upstream area of the mixing chamber. In other words, the flow paths or channels leading from the inlet connections into the mixing chambers are preferably designed in such a way that one of the components substantially arrives in the mixing chamber in radial direction and the other component substantially in axial direction, as a result of which a good mixing takes place already when the components coming from different flow directions meet each other.

The plate provided at the mixer element is intended to, on the one hand, prevent that the component tending to bleed arrives in the mixing chamber directly, and on the other hand, that this component can continue to flow into the mixing chamber after the annular chamber has been actively filled by the rotational motion, without significantly increasing the flow resistance within the mixer. For this, it is preferred when at least one opening is formed in the plate that connects the annular reservoir chamber with the mixing chamber. Preferably, several recesses are provided, in particular, at the radially outer area of the plate.

In order to further improve the distribution of the components tending to bleed forward within the annular reservoir chamber, carriers are designed at the mixer element or the plate. These carriers can be designed as bars or walls extending transverse to the plate of the mixer element. Preferably, these types of carriers are provided on both sides of the at least one opening connecting the annular reservoir chamber and the mixing chamber. This has the further advantage than upon turning the mixer off, a subsequent flow or a back-flow of one component into the inlet connection of the other component as the result of pressure fluctuations can be avoided. Hereby, the risk of a so-called reverse contamination is minimized.

The active filling of the annular reservoir chamber by the rotary motion and a minimization of the flow resistance within the mixer can be achieved thereby, that the annular reservoir chamber is designed as cylindrical cavity that is interspersed in sections by a cylindrical mixer element. Thus, in a longitudinal cross section of the mixer, the annular reservoir chamber can be designed nearly rectangular and be preferably interspersed with the cylindrically designed section of the mixer element.

According to a preferred embodiment of the invention, the mixer housing has a first cylindrical section surrounding the mixing chamber that is, for example, conically tapered toward the outlet opening. In order to be able to provide a sufficiently large volume for the annular reservoir chamber, preferably, a second cylindrical section is provided at the mixer housing, which houses the cover. Thereby, the first cylindrical section is preferably connected with the second cylindrical section by a radially extending wall.

Especially in the previously cited embodiment with the radially extending wall between two cylindrical sections of the mixer housing, the gasket seal between the cover and the mixer housing can be surfaces that are opposite to each other in axial direction. Preferably, a labyrinth seal is provided for this, for example, in the form of a surrounding annular channel in the cover, with which an annular surrounding bar of the mixer housing engages. Hereby, it is preferred when the cover is initially only retained freely rotatable in the mixer housing, for example, by a snap-on connection, whereby the gasket seal is not yet required to seal completely. As a result of the screw fastening of the mixer at a cartridge, the cover is pressed firmly against the mixer housing only when the mixer is used, as a result of which the gasket seals. The final sealing of both parts thus takes place only by screwing the outer thread of the mixer into the corresponding inner thread of the cartridge.

A particularly good seal can be established thereby, that the cover and the mixer housing consist of materials having a different hardness. For example, the cover can consist of a softer material, for example, polypropylene (PP) or polyethylene (PE), and the mixer housing of a harder material, for example, polyoxymethylene (POM), in particular, highly transparent polyethylene terephthalate (PET), polymethyl methacrylate (PMMA) or polycarbonate (PC). Preferably, the mixer element consists of POM or a plastic having similar properties that likewise makes a good seal possible relative to the softer cover.

Preferably, the cover of the mixer is freely rotatable and axially fixated in the mixer housing. The mixer element is likewise freely rotatable and preferably mounted axially fixated in the mixer housing and the cover. This design of the mixer with a freely rotatable cover relative to the mixer housing makes a number of different ways of mounting the mixer possible, for example, at a cartridge system.

Thus, it is considered to be especially advantageous when the mixer housing has a thread in sections of its outer side. This, preferably, self-locking thread makes it possible to screw the mixer housing into a corresponding inner thread of a cartridge system, whereby the inlet connections of the cover overlap with corresponding outlet connections of the cartridge system, or can be engaged. In this way, the mixer can easily be screwed onto a cartridge system, or can be removed from such by being screwed off.

The cartridge and the mixer can be equipped with catch elements that engage with each other when the threads of the mixer and the cartridge are screwed into each other. On the one hand, this can prevent an unintentional separation of the mixer from the cartridge, and on the other hand, give a tactile and/or acoustic confirmation to the user that the mixer is properly mounted.

In order to improve the alignment of the cover when connecting the mixer with a cartridge system, the cover is preferably designed integral with at least one positioning latch extending parallel to the inlet connections. This positioning latch can, preferably even before the inlet connections come in contact with the outlet connections of the cartridge system, engage with a corresponding opening of the cartridge system in order to thereby ensure the correct alignment of the mixer relative to the cartridge system, specifically, the entry of the mixer with the exit of the cartridge.

Preferably, on the front of a radial wall of the mixer housing, wing screws are provided to facilitate the fastening or removal of the mixer from a cartridge. To avoid a delay, the wing screws in the housing are preferably only fastened at the radial wall, i.e. at a distance from the cylindrical wall of the mixing chamber.

The attaching or detaching of the mixer from a cartridge can also, or alternatively, be facilitated by a fluting or knurling. The fluting and/or knurling is preferably formed by channels (instead of projecting ribs) for haptic reasons.

Further, the mixer element can be provided with a threading geometry, which facilitates the insertion of a drive shaft into the mixer element. This can, for example, be a conical bevel or other incline facilitating a catch and automatically aligning the hexagonal socket of the mixer element and the drive shaft having the hexagonal head upon insertion.

It is preferred when the second of the two inlet connections leads into the mixing chamber via a channel that is guided laterally or in parallel past the annular reservoir chamber, or through such.

In the following, the invention will be explained in further detail with the help of an exemplary embodiment and by referring to the drawing. Thereby, all described and/or illustrated features by themselves constitute the subject matter of the invention, regardless of their summary in the claims or their references.

Schematically shown are:

FIG. 1 shows a perspective view of a mixer according to the invention.

FIG. 2 shows an exploded view of the components of the mixer according to FIG. 1.

FIG. 3 shows a further exploded view of the components of the mixer according to FIG. 1.

FIG. 4 shows the cover and the mixer element of the mixer according to FIG. 1 in a perspective view.

FIG. 5 shows a partial cross section of the mixer according to FIG. 1 in a perspective view, FIG. 6 shows a lateral view of the mixer according to FIG. 1.

Figure 7:
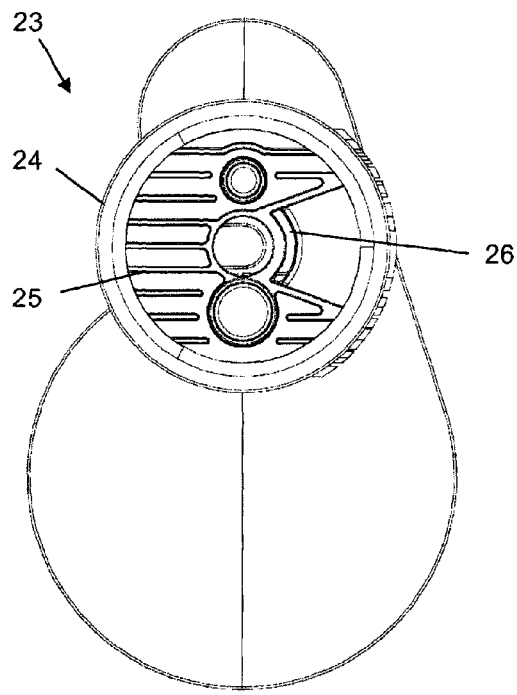
FIG. 7 shows a cartridge for use with a mixer according to the invention.

Mixer 1 according to the invention that is shown in the Figures is a dynamic mixer consisting of a mixer housing 2, a cover and a mixer element 4.

Mixer housing 2 has a first cylindrical section 5 that is tapered to an outlet opening 6—at the left end in FIG. 1. From the first cylindrical section 5, a radially extending flange-like wall 7 branches off connecting first cylindrical section 5 with a second cylindrical section 8. Second cylindrical section 8 thereby has a larger diameter than first cylindrical section 5.

On the outer surface of second cylindrical section 8, thread segments 9 are provided, which form an outer thread for screwing mixer 1 onto a cartridge system 23 that is shown in FIG. 7. On the side facing away from outlet opening 6 of radial wall 7, an annularly surrounding bar 10 is formed, which forms a component of a gasket seal relative to cover 3 as will be described in further detail below. Further, on the inner side of second cylindrical section 8, catch elements 11 are formed for connecting mixer housing 2 with cover 3.

On its right side in FIG. 1, cover 3 has two inlet connections 12, 13 for the components that are to be mixed. Inlet connections 12, 13 have a different diameter in the illustrated embodiment so that components having a different volume ratio can be mixed with each other. Deviating from the illustration in the Figures, it is also possible to process other volume ratios or identical volume ratios by correspondingly adapting the geometry of the inlet connections into a mixer.

Parallel to inlet connections 12, 13, a positioning latch 14 projects from the right side of cover 3 in FIG. 1, the length of which is longer than that of inlet connections 12, 13. Positioning latch 14 is thereby designed arched in cross section, so that inlet connections 12, 13 automatically meet the outlet connections of a cartridge 23 when positioning latch 14 is inserted into a correspondingly designed opening 26 of the cartridge. FIG. 7 also shows a ring 24 that is provided in the outlet area of cartridge 23, which has an inner thread for connecting with thread segment 9. On a plate surrounded by this ring 24, in which the outlet connections of cartridge 23 end, protruding ribs 25 are formed opposite to the plate in the direction of the mixer, which prevent an erroneous attachment of the mixer. Beyond that, such a transverse ribbing between and/or underneath the outlet connections of the cartridge, an undesired carryover, for example, of the catalytic paste, or the base paste of a two-component mixture to the respectively other channel, can be avoided.

The following steps are required for attaching a mixer 1 according to the invention to a cartridge 23: First, positioning latch 14 comes in contact with the corresponding adapter at the cartridge, starting at a certain point, whereby at the beginning, there is some play between positioning latch 14 and adapter 26 in the cartridge. Thereafter, the positioning latch functions like a guide track in a, for example, conically tapered channel of the cartridge. As a consequence, mixer 1 is hereby centered and aligned automatically in cartridge 23 due to the axial insertion of the positioning latch 14.

At the outer peripheral surface of cover 3, a catch lip 15 is formed which works together with catch elements 11 of mixer housing 2 for attaching cover 3 to mixer housing 2. In this way, cover 3 can be fixated freely rotatable, but axially fixed within mixer housing 2.

In cover 3, a central through hole is formed that is surrounded by a collar 16, which forms a friction bearing for mixer element 4. As can be seen especially clearly in FIGS. 2 and 4, an essentially cylindrical free space is also provided in cover 3, which surrounds collar 16 in sections. In mixer 1, this free space forms, among other things, an annular reservoir chamber 17. The diameter of the free space and the position of inlet connection 13 are selected in such a way that the free space and the opening of inlet connection 13 partially overlap in axial direction. A component flowing in through inlet connection 13 can thus at least partially arrive in annular reservoir chamber 17 without any redirection. This component then arrives in the mixing chamber in axial direction. On the other hand, as can be seen especially clearly in FIG. 6, channel-like extended inlet connection 12 ends with a radial opening directly in an area that is a part of the mixing chamber of the cylindrical free space of cover 3.

Mixer element 4 is designed as drivable mixer rod, which is designed—at its right end in FIG. 1—as a hollow shaft with a hexagonal socket, with which a hexagonal drive shaft can engage. The section of mixer element 4 that is rotatable in collar 16 of cover 3 is designed cylindrical in sections.

Further, a circular plate 18 extending radially off mixer element 4 is provided. As can be seen, for example, in FIGS. 2 and 9, the radial outer section of plate 18 has four annular-segment-like recesses 19, which respectively extend by somewhat less than 90°. In the area of the bars of plate 18 that remain between recesses 19, carriers 20 are formed, which are designed as walls extending perpendicular to plate 18.

Figure 8:
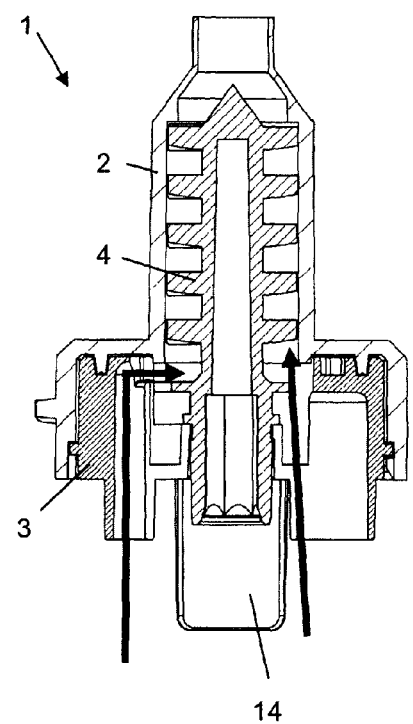
FIG. 8 shows the flow paths of the components in a mixer according to the invention.

In the assembled condition of mixer 1, plate 18 defines a boundary wall for mixing chamber 17, which is formed in cover 13. Hereby, the position of plate 18 on mixer element 4 is selected in such a way that only the component that Is conveyed into the annular reservoir chamber 17 via inlet connection 13 arrives there exclusively, is actively distributed there and flows from there into the mixing chamber. In contrast, the component arriving in the mixer via inlet connection 12 on the opposite side of plate 18, is conveyed radially into the mixing are of mixer 1, which is substantially enclosed by the first cylindrical section 5 of mixer housing 2. Thus, plate 18 separates annular reservoir chamber 17 from the mixing chamber and makes a fluid communication with annular reservoir chamber 17 and the mixing chamber possible because of recesses 19. As shown in FIG. 8, the inflow of components takes place orthogonally to each other, as a result of which good mixing is achieved without noticeably increasing the flow resistance.

Further, at mixer element 4, arms 21 are located at several levels that serve to mix the two components in the mixing chamber.

In the assembled condition of mixer 1, mixer element 4 is freely rotatable in cover 3, whereby the section of mixer element 4 that is provided with arms 21 is housed in first cylindrical section 5 of mixer housing 2. Cover 3 is attached freely rotatable to mixer housing 2, as catch lip 15 of catch elements 11 of mixer housing 2 is engaged. A gasket seal between mixer housing 2 and cover 3 takes effect via annular bar 10 of mixer housing 2, which engages with a corresponding groove 22 in cover 3 in the manner of a labyrinth seal that engages then, when a mixer is screwed into the cartridge in positive mode.

In this assembled condition of the mixer, plate 18 of mixer element 4 is in a position that the two components entering through inlet connections 12 and 13 arrive at mixer element 4 at opposite sides of plate 18, i.e. at levels that are offset to each other in axial direction of the mixer. The component entering through the larger inlet connection 13 shown in the illustrated example, thereby first arrives in annular reservoir chamber 17, whereby this component is distributed by the rotation of carriers 20 together with mixer element 4 in annular reservoir chamber 17 in such a way that it fills up. The rotation of mixer element 4 thus has the effect of an active filling of annular reservoir chamber 17, in particular, also regardless of a potential counter pressure within mixer 1.

When annular reservoir chamber 17 is at least mostly filled, the component flowing in through inlet connection 13 also arrives in the mixing chamber through recesses 19. This component thus enters the mixing chamber in axial direction. In contrast, the component fed through inlet connection 12 enters the mixing chamber in radial direction as a result of which the two components are mixed well from the start. This mixing is further intensified by arms 21 that rotate with mixer element 4, so that a homogenous mixture of the two component discharges from outlet opening 6.

Figure 10:
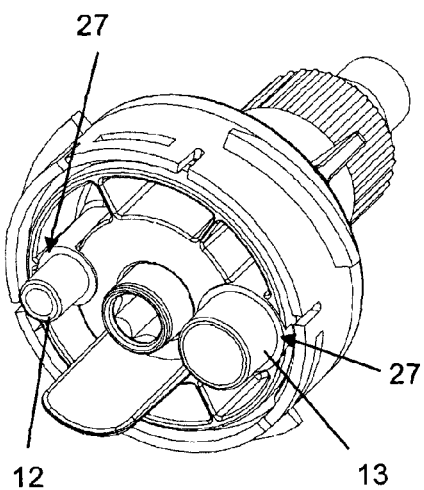
FIG. 10 shows a further embodiment of a mixer in a perspective view.
Figure 11:
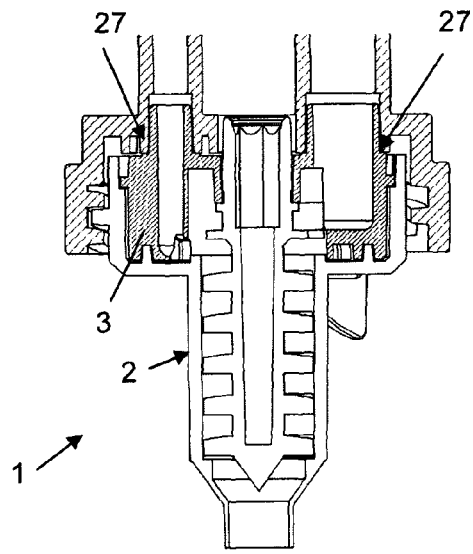
FIG. 11 shows the mixer according to FIG. 13 in cross section in a cartridge system.

The mixer shown in FIGS. 10 and 11 has annular, frontal sealing surfaces 27 at cover 3, which are provided around inlet channels 12, 13, and on which the respective outlet connection of the cartridge comes to rest. These sealing surfaces have an additional frontal sealing effect relative to the radial sealing surface at the outer circumference of the connectors.

Figure 12:
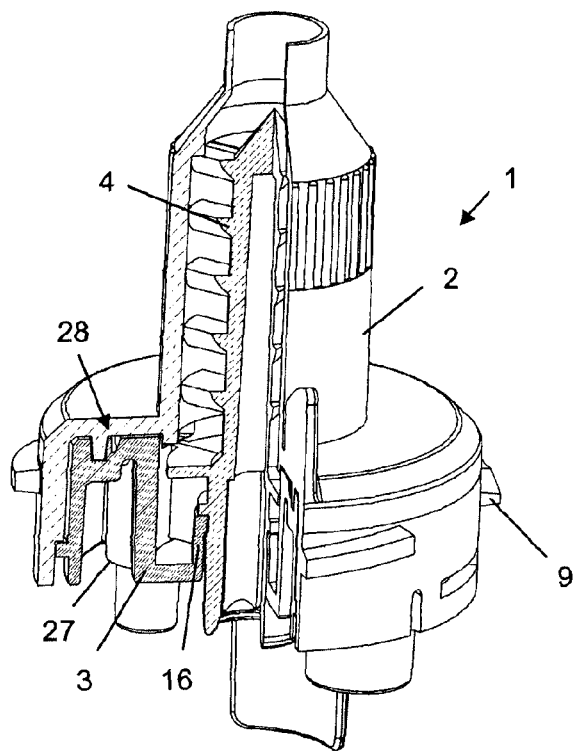
FIG. 12 shows a further embodiment of the mixer in partial cross section in a perspective view and FIG. 13 shows the mixer element of the mixer according to FIG. 12.
Figure 13:
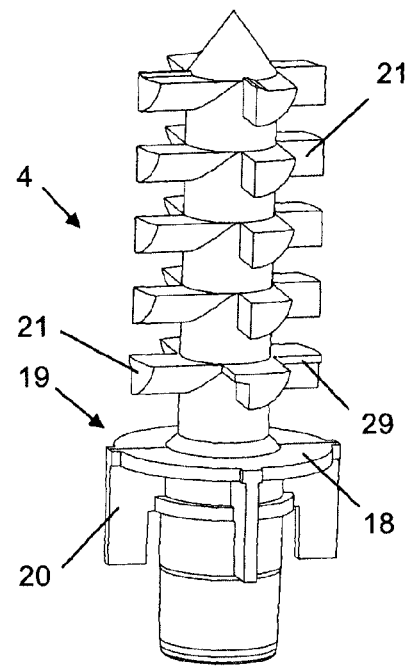

A further embodiment of the mixer according to the invention is shown in FIGS. 12 and 13. Different than the mixer according to FIGS. 10 and 11, it has an annular sealing lip 28 at cover 3 on the radial inner side of bar 10, which has the effect of an improved gasket seal at high pressure. Additionally, mixer element 4 is designed differently compared with the embodiment in FIG. 9. In particular, carriers 20 are designed elongated at plate 18 in the direction toward the cartridge, so that annular reservoir chamber 17 in FIG. 12 is essentially completely closed downward. Thus, any cross contamination, i.e. an undesired flow of one component into the inlet area of the other component can be avoided even more effectively.

In mixer element 4 according to FIG. 13 even arms 21 of the first arm level (in FIG. 13 bottom) facing plate 18 are designed differently than arms 21 of the other levels. Thus, at arms 21, at their vertical front side (front in the direction of rotation), a horizontal wall 29 is provided respectively that makes penetration of the components into the mixing chamber more difficult or slower. Hereby, a more intensive mixing of the two components takes place in the area in which the channel of inlet connection 12 ends in the mixing chamber.

Figure 9:
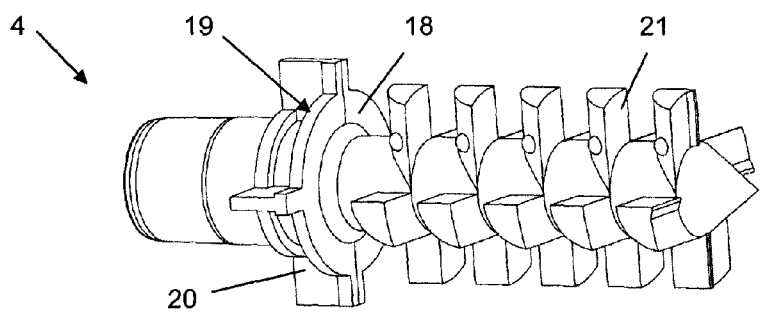
FIG. 9 shows the mixer element of a mixer according to the invention in a perspective view.

Different than the illustration shown in FIGS. 9 and 13, it can be advantageous for a better mixing homogeneity when a further mixing blade or mixer element is installed at the upper (on the side of the outlet) end of mixer element 4 in the direction of the mixer outlet that follows the contour of the tapered mixer shell and projects into the mouth of the mixer, where FIGS. 9 and 13 have a pointed cone.

The advantages of the mixer according to the invention are also given by the following comparative examples:

The measured values in Table 1 show that the measured discharge forces when using the dynamic mixer optimized for flow according to the invention, are significantly below the values measured for the same impression materials using dynamic mixers according to prior art.

TABLE 1

Discharge forces of two-component impression materials out of 380 ml cartridges (mixing ratio of catalytic paste to base paste: 1:5) using various dynamic mixers[1]

| Examples | medium body impression material[2] | heavy body impression material[3] | putty impression material[4] |
|---|---|---|---|
| System according to the invention | 1550N | 1950N | 6000N |
| Comparative example 1 | 2400N | 2600N | 7000N |
| Comparative example 2 | [5] | [6] | [7] |
| Comparative example 3 | 1900N | 2450N | 6100N[8] |

Comparative example 1: Sulzer Mixpac System, Mixer MBD 381-05-HS, Article No. 116211, Lot No. SO04105 (according to EP 1 943 012)
Comparative example 2: DMG System (according to DE 10 2004 008 748)
Comparative example 3: Zhermack System (according to EP 1 892 033)
[1]For this, the cited impression materials were filled into the respective cartridge/mixer system and the discharge forces were captured by a corresponding measurement unit of the universal test machine Zwick Z 0100 at a feed rate of 46 mm/min while rotating the dynamic mixer at 700 U/min.
[2]Identium medium, Kettenbach GmbH & Co. KG, Type 2 according to ISO 4823, Lot 110191-60
[3]Identium heavy, Kettenbach GmbH & Co. KG, Type 1 according to ISO 4823, Lot 120211-36
[4]Aquasil Deca putty, Dentsply DeTrey Inc., Type 0 according to ISO 4823, Lot 607510
[5]This cartridge/mixer combination is not suitable for discharging medium consistencies. In particular, the mechanical stability of the cartridge insufficiently absorbs the forces generated. The cartridge burst at 5300N.
[6]This cartridge/mixer combination is not suitable for discharging heavy consistencies. In particular, the mechanical stability of the cartridge insufficiently absorbs the forces generated.
[7]This cartridge/mixer combination is not suitable for discharging putty consistencies. In particular, the mechanical stability of the cartridge insufficiently absorbs the forces generated.
[8]At the measured discharge forces, leaks appeared at the mixer and in the area of the locking stoppers.

The measurement values in Table 2 show that when the dynamic mixer according to the invention is used, the material selected for the labyrinth seal between the mixer sleeve (PET) and mixer cover (PP) and the bearing at the seal of the mixer rod (POM) in the cylinder sleeve in mixer cover (PP), lead to a very good imperviousness relative to dynamic mixers according to prior art. The measured values further show that in dynamic mixers according to prior art, the imperviousness becomes acceptable only after costly technical steps, for example, by integrating an O-ring seal in the area of the mixer rod relative to the mixer cover (see comparative examples Zhermack 2009 with Zhermack 2012) or by integrating ultrasonic welding between the mixer cover and the mixer sleeve (see comparison of examples Sulzer Mixpac 2008 with Sulzer Mixpac 2011). The selection of highly transparent PET for the mixer sleeve is possible, because in the mixer according to the invention, no ultrasonic welding is required between the mixer cover and the mixer sleeve. The high transparency leads to an opportunity of good visual control in the mixer during the mixing process.

TABLE 2

Imperviousness and transparency of various dynamic mixers[1] during the discharge of two-component dental impression materials out of 380 ml cartridges (mix ratio catalytic paste to base paste: 1:5):

| Examples | Material combination mixer rod cover sleeve | Sealing principle sleeve to cover | Evaluation transparency[1] sleeve | Evaluation impermeability[2] sleeve cover | Evaluation impermeability[2] cover mixer rod |
|---|---|---|---|---|---|
| Mixer according to the invention | POM-PP-PET | Labyrinth seal freely rotatable via screw connection of the mixer in the cartridge, sealing | ++ | ++ | ++ |
| Comparative example 1 | POM-PP-PP | Interlocked, not rotatable | o | -- | + |
| Comparative example 2 | POM-PP-PP | Ultrasonically welded, not rotatable | o | ++ | ++ |
| Comparative example 3 | POM-PP-PP | double interlock, not rotatable | o | + | -- |
| Comparative example 4 | POM-PP-PP | quadruple interlock, not rotatable, O-ring-gasket at the mixer rod | o | + | ++ |

Comparative example 1: Sulzer Mixpac System 2008, Article: MDB 381-05-00 (according to EP 1 943 012)
Comparative example 2: Sulzer Mixpac System 2011, Article: MDB 381-05-HS (according to EP 1 943 012)
Comparative example 3: Zhermack System 2009 (according to EP 1 892 033)
Comparative example 4: Zhermack System 2012 (according to EP 1 892 033)
[1]For this, the impression material Identium medium was filled into the respective cartridge/mixer system and discharged and mixed for one minute with a conventional delivery device (Renfert Sympress II) having a feed rate of 46 mm/min and a mixer speed of 700 U/min. The imperviousness of the respective dynamic mixer was evaluated visually at the seal of mixer rod to mixer cover and at the seal of mixer sleeve to mixer cover with the help of a scale from ++ to --: ++: very good, no discharge of mass +: little discharge of mass o: significant, still acceptable discharge of mass -: strong discharge of mass --: strong discharge of mass with contamination of the discharge device/the
[2]For this, the impression material Identium medium was filled into the respective cartridge/mixer system and discharged and mixed for one minute with a conventional delivery device (Renfert Sympress II). The high transparency makes it possible for the user to use optimal visual mixing control. The transparency of the respective plastic was evaluated visually at the mixer sleeve with the help of a scale ranging from ++ bis --: ++: highly transparent, mass can be clearly identified +: transparent, slight clouding, mass easily identifiable o: significant clouding, mass shines through -: strong clouding, mass still identifiable --: not transparent, mass cannot be identified The measured values in Table 3 show that when using the dynamic mixer according to the invention, the annular reservoir chamber fills completely at a significantly faster rate than the accumulation chambers in dynamic mixers according to prior art. This eliminates the risk that over the course of the subsequent process of mixing—when the counter pressure in the mixer rises—volume dosage fluctuations arise due to tardy filling in the accumulation chamber, which leads to non-homogeneities in the mixture in the discharged product.

TABLE 3

Comparison of the various dynamic mixers with respect to the fill levels of the accumulation chamber at various points in time after the start of mixing, compared with the mixer according to the invention with an annular reservoir chamber.[1]

| Example | 1 s | 1.5 s | 2 s | 2.5 s | 3 s | 4 s |
|---|---|---|---|---|---|---|
| System according to the invention | 70% | 100% | 100% | 100% | 100% | 100% |
| Comparative example 1 | 10% | 20% | 40% | 50% | 90% | 100% |
| Comparative example 2 | 30% | 50% | 70% | 80% | 100% | 100% |

Comparative example 1: Sulzer Mixpac System (according to EP 1 943 012)
Comparative example 2: DMG System (according to DE 10 2004 008 748)
[1]For this, a dental impression material with average flow properties, Type 2 according to ISO 4823, was filled into the respective cartridge/mixer system and discharged using a Sympress I - delivery device made by Renfert, and mixed by using the respective dynamic mixer. The fill level of the respective accumulation/annular reservoir chamber was visually evaluated by stopping the mixing processes after 1 s, 1.5 s, 2 s, 2.5 s, 3 s and 4 seconds.

Reference numbers:

| 1 | Mixer |
|---|---|
| 2 | Mixer housing |
| 3 | Cover |
| 4 | Mixer element |
| 5 | First cylindrical section of the mixer housing |
| 6 | Outlet opening |
| 7 | Wall |
| 8 | Second cylindrical section of the mixer housing |
| 9 | Thread segment |
| 10 | Bar |
| 11 | Catch element |
| 12 | Inlet connection |
| 13 | Inlet connection |
| 14 | Positioning latch |
| 15 | Catch lip |
| 16 | Collar |
| 17 | Annular reservoir chamber |
| 18 | Plate |
| 19 | Recess |
| 20 | Carrier |
| 21 | Arm |
| 22 | Groove |
| 23 | Cartridge |
| 24 | Ring |
| 25 | Rib |
| 26 | Opening |
| 27 | Facing sealing surfaces |
| 28 | Lip |
| 29 | Wall |

What is claimed is:

1. A mixer for mixing two components, in particular, a hardenable dental material having
 a mixer housing that has a mixing chamber with an outlet opening,
 a mixer element that extends in the mixing chamber,
 a cover having two inlet connections for the components that is connected with the mixer housing, and
 an annular reservoir chamber that is in fluid communication with the mixing chamber,
 wherein the annular reservoir chamber is a reservoir chamber that is defined by the cover and a plate that is provided on the mixer element, and
 that the first of the two inlet connections ends upstream of the plate in the annular reservoir chamber, and
 the second of the two inlet connections ends outside of the annular reservoir chamber and downstream of the plate in the mixing chamber.

2. A mixer as recited in claim 1, wherein the annular reservoir chamber and the first inlet connection ending in it overlap at least partially in an axial direction, and wherein the second inlet connection ends in the mixing chamber in a radial direction.

3. A mixer as recited in claim 1, wherein the flow paths leading from the inlet connections into the mixing chamber are designed in such a way that one of the components enters the mixing chamber in an essentially radial direction and the other component in an essentially axial direction.

4. A mixer as recited in claim 1, wherein at least one opening that connects the annular reservoir chamber with the mixing chamber is formed in the plate.

5. A mixer as recited in claim 1, wherein at the mixer element, in particular, at the plate, carriers are formed to actively carry along and distribute a component within the annular reservoir chamber.

6. A mixer as recited in claim 1, wherein the annular reservoir chamber is designed as a cylindrical cavity that is interspersed in sections by the cylindrical mixer element.

7. A mixer as recited in claim 1, wherein the mixer housing has a first cylindrical section surrounding the mixing chamber that is conically tapered toward the outlet opening, and a second cylindrical section housing the cover, whereby the first cylindrical section is connected with the second cylindrical section by a radially extending wall.

8. A mixer as recited in claim 1, wherein between the cover and the mixer housing, a labyrinth seal is located in surfaces opposite to each other in an axial direction.

9. A mixer as recited in claim 1, wherein the cover can be rotated freely and is housed axially fixated in the mixer housing.

10. A mixer as recited in claim 1, wherein the mixer housing is completely or partially covered by a thread on its outer side.

11. A mixer as recited in claim 1, wherein the cover is designed integral with at least one positioning latch that extends parallel to the inlet connections.

12. A mixer as recited in claim 1, wherein the cover comprises a first material, in particular, polypropylene (PP), and the mixer housing and/or the mixer element comprises a second material having a different hardness than the first material, in particular, polyethylene terephthalate (PET) or polyoxymethylene (POM).

13. A mixer as recited in claim 1, wherein screw wings are provided on a front of a radial wall of the mixer housing.

14. A mixer as recited in claim 1, wherein a fluting and/or knurling is formed by grooves on the mixer housing.

15. A mixer as recited in claim 1, wherein the mixer element is provided with a mounting geometry that facilitates the insertion of a drive shaft into mixer element.

16. A mixer as recited in claim 1, wherein the second of the two inlet connections ends in the mixing chamber via a channel that goes laterally past or passes through the annular reservoir.

* * * * *